United States Patent
Zhang et al.

(10) Patent No.: US 11,161,818 B2
(45) Date of Patent: Nov. 2, 2021

(54) QUINOLONE DERIVATIVES, PREPARATION METHODS AND APPLICATION THEREOF

(71) Applicant: Hangzhou Normal University, Zhejiang (CN)

(72) Inventors: Pengfei Zhang, Zhejiang (CN); Wanmei Li, Zhejiang (CN); Weiming Xu, Zhejiang (CN); Haifeng Wu, Zhejiang (CN)

(73) Assignee: HANGZHOU NORMAL UNIVERSITY, Zhejiang (CN)

( * ) Notice: Subject to any disclaimer, the term of this patent is extended or adjusted under 35 U.S.C. 154(b) by 0 days.

(21) Appl. No.: 16/828,446

(22) Filed: Mar. 24, 2020

(65) Prior Publication Data
US 2021/0198207 A1 Jul. 1, 2021

(30) Foreign Application Priority Data
Dec. 30, 2019 (CN) .......................... 201911400744.1

(51) Int. Cl.
*C07D 215/56* (2006.01)

(52) U.S. Cl.
CPC .................................. *C07D 215/56* (2013.01)

(58) Field of Classification Search
CPC ..................................................... C07D 215/56
USPC ........................................................... 514/312
See application file for complete search history.

(56) References Cited

U.S. PATENT DOCUMENTS 8,389,545 B2 * 3/2013 Shipe ..................... A61P 25/20
514/312

OTHER PUBLICATIONS

Yingjie et al., "Design,Synthesis and Anti-tumor Activity of Levofloxacin-Ligustrazine Conjugates", Acta Med Univ Sci Technol Huazhong, Aug. 2018, vol. 47, 7 pages.
Ke et al., "Synthesis and anti-tumor activities of new histone deacetylase inhibitor-gatifloxacin conjugates", China Academic Journal Electronic Publishing House, Jul. 12, 2018, 9 pages.

* cited by examiner

*Primary Examiner* — Rita J Desai

(57) ABSTRACT

A novel quinolone derivative and methods of its preparation are described in which the novel derivative comprises a diphenyl ether substituent on the nitrogen atom at the 1-position of the main quinolone ring. The novel derivative is shown to have antibacterial and anti-tumor cell activity.

12 Claims, No Drawings

QUINOLONE DERIVATIVES, PREPARATION METHODS AND APPLICATION THEREOF

TECHNICAL FIELD

The present disclosure relates to new quinolone derivatives, preparation methods and application thereof.

BACKGROUND

Since fluoroquinolones came out in 1962, after decades of development, they have been continuously updated and improved, forming the second, third and fourth generation of fluoroquinolones, which have many advantages, such as broad antibacterial spectrum, strong bactericidal activity, low toxicity and high efficacy and are widely used in clinical treatment of various bacterial infections. In the past decade, through structural modification, it has been found that these compounds also have many other biological activities, e.g., progress has been made in studies on anti-tumor, anti-virus, anti-anxiety and so on, and some candidate compounds have entered clinical research stage. Quinolones are inhibitors of bacterial topoisomerase II. It has been found that there is homology between bacterial topoisomerase II and mammalian topoisomerase II in the sequence around the active site tyrosine, and some quinolones have strong inhibitory effect on mammalian topoisomerase II. At present, hundreds of quinolones with anti-tumor activity have been reported through structural modification, which may become a new type of anti-tumor drugs targeting at topoisomerase II. Therefore, the design of novel anti-tumor drugs based on quinolones has become a hot field of tumor chemistry.

Lu Yingjie, et al. [*Journal of Huazhong University of Science and Technology (Medical Sciences)*, 2018, 47, 4, 410-416] designed and synthesized conjugates of levofloxacin and tetramethylpyrazine, and studied its inhibition of tubulin polymerization and anti-tumor activity. Levofloxacin was used as raw material, and the tetramethylpyrazine unit was introduced into the carboxyl group at the C3 position of levofloxacin. The inhibitory activity of the synthesized target conjugate on tubulin polymerization and the activity against five tumor cells of A549, HepG2, MCF7, MDAMB231 and PC3 in vitro were tested by tubulin polymerization kit and MTT method. The results of preliminary bioassays showed that the synthesized levofloxacin tetramethylpyrazine conjugates had the same inhibitory effect on tubulin polymerization as the positive drug, colchicine, and had strong inhibitory activity on the five tumor cells of A549, HepG2, MCF7, MDAMB231 and PC3. At the same time, none of these levofloxacin tetramethylpyrazine conjugates were toxic to normal mammary epithelial cells MCF10A. Therefore, tetramethylpyrazine is an anti-tumor pharmacophore, which can enhance the anti-tumor activity of quinolones.

Yang Ke, et al. [*Chinese Journal of Antibiotics*, 2019, 44, 7811-819] designed and synthesized gatifloxacin-histone deacetylase inhibitor (HDACi) conjugates with quinolone as the parent, and discussed their anti-tumor activity. Gatifloxacin was used as raw material, and the structure thereof was modified by introducing a suberoylanilide hydroxamic acid (SAHA) into C-7 piperazinyl group and C-3 carboxyl group, respectively. The activity of enzyme and anti-tumor activity of the conjugates were tested by HDACs kit, tubulin kit and MTT method. The preliminary bioactivity studies showed that the target compound could effectively inhibit tubulin polymerization and HDACs. Among these, conjugates 10b and 13, in which the side chain of the SAHA analog unit is 6 methylene groups, have stronger inhibitory and anti-tumor activities on tubulin polymerization and HDACs than other derivatives. Therefore, the introduction of histone deacetylase inhibitor (HDACi) unit to gatifloxacin can improve its anti-tumor activity.

Under this background, the disclosure modifies the structure of quinolone by derivatizing the substituent on the nitrogen atom at position 1 and introducing a diphenyl ether structure unit with biological activity to form new quinolone derivatives, and studies the anti-tumor activity thereof.

SUMMARY

The technical problem to be solved by the disclosure is to introduce a diphenyl ether structure unit at position 1 of the main ring of quinolone, and at the same time appropriately change positions 3, 6 and 7 of the main ring to obtain a class of structurally new quinolone derivatives with anti-tumor activity, and the preparation method thereof is disclosed.

The technical solution employed by the present disclosure is as follows:

A new quinolone derivative, the structure of which is shown in formula (I):

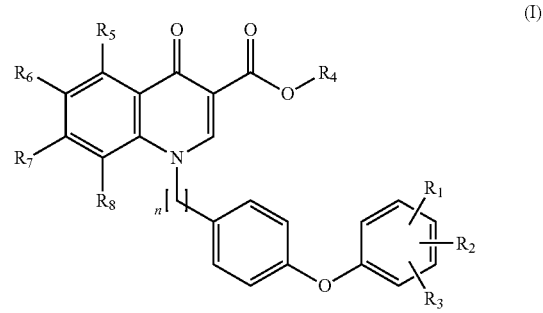

(I)

wherein n represents a number of 0 or 1; $R_1$, $R_2$ and $R_3$, which are independently of each other, represent hydrogen, a C1-C6 alkyl group, a C1-C6 alkoxy group, a C5-C6 cycloalkyl group, a C1-C6 alkyloxy group, a C1-C6 hydroxyalkylene group, a C1-C6 alkylmercapto group, a C1-C6 mercaptoalkylene group, a C1-C6 alkylamino group, halogen, a hydroxy group, a mercapto group, a cyano group, a nitro group, a trifluoromethyl group, a trifluoromethoxy group, a difluoromethyl group, a difluoromethoxy group, a monofluoromethyl group, a monofluoromethoxy group;

$R_4$ is selected from hydrogen, a C1-C6 alkyl group, a C5-C6 cycloalkyl group, a phenyl group, a substituted phenyl group, a benzyl group or a substituted benzyl;

$R_5$, $R_6$, $R_7$ and $R_8$ are hydrogen, a C1-C3 alkyl group, halogen, a cyano group or a nitro group.

Preferably, the structure thereof is shown in formula (I-a):

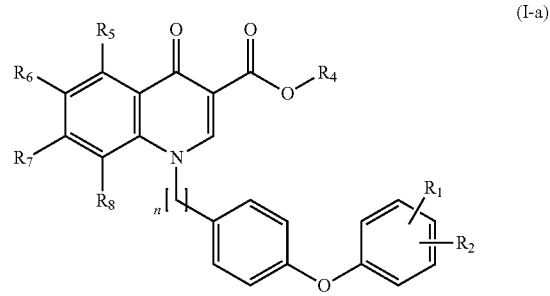

(I-a)

wherein n represents a number of 0 or 1;

$R_1$, $R_2$, which are independently of each other, represent hydrogen, a C1-C6 alkyl group, a C1-C6 alkoxy group, a C5-C6 cycloalkyl group, a C1-C6 alkyloxy group, a C1-C6 hydroxyalkylene group, a C1-C6 alkylmercapto group, a C1-C6 mercaptoalkylene group, a C1-C6 alkylamino group, halogen, a hydroxy group, a mercapto group, a cyano group, a nitro group, a trifluoromethyl group, a trifluoromethoxy group, a difluoromethyl group, a difluoromethoxy group, a monofluoromethyl group, a monofluoromethoxy group;

$R_3$ represents hydrogen;

$R_4$ is selected from hydrogen, a methyl group, an ethyl group, a n-propyl group, an isopropyl group, a n-butyl group, an isobutyl group, a tert-butyl group, a phenyl group;

$R_5$, $R_6$, $R_7$ and $R_8$ are hydrogen, halogen, a cyano group or a nitro group.

More preferably, the structure thereof is shown in formula (I-b):

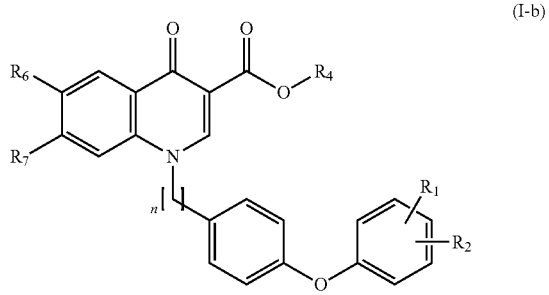

(I-b)

wherein n represents a number of 0 or 1;

$R_1$, $R_2$, which are independently of each other, represent hydrogen, a C1-C6 alkyl group, a C1-C6 alkoxy group, halogen, a cyano group, a nitro group, a trifluoromethyl group, a trifluoromethoxy group, a difluoromethyl group, a difluoromethoxy group;

$R_4$ is selected from hydrogen, a methyl group, an ethyl group;

$R_5$, $R_8$ represent hydrogen;

$R_6$ is fluoro;

$R_7$ is chloro.

The second technical problem to be solved by the present disclosure is to provide a method for preparing the new quinolone derivatives, which is illustrated as follows with detail:

a) reacting formula (II) with water in an organic solvent under the catalysis of a Lewis acid to obtain an intermediate product A;

b) adding an acid binding agent ① to the reaction system, mixing it with the raw material shown in formula (III) for reaction, then adding a diphenyl ether amine compound shown in formula (IV) for reaction to obtain an intermediate product B;

c) adding a further acid binding agent ② and a supported catalyst to carry out a cyclization reaction to obtain the target compound of formula (I).

Dimethylamine, a by-product of the reaction, is absorbed by carbon dioxide to form dimethylamine carbon dioxide complex (VI). In the presence of a liquid base, the complex reacts with sodium formyl acetate (VII) to obtain formula (III) again, realizing the recycling of dimethylamine See Scheme 1.

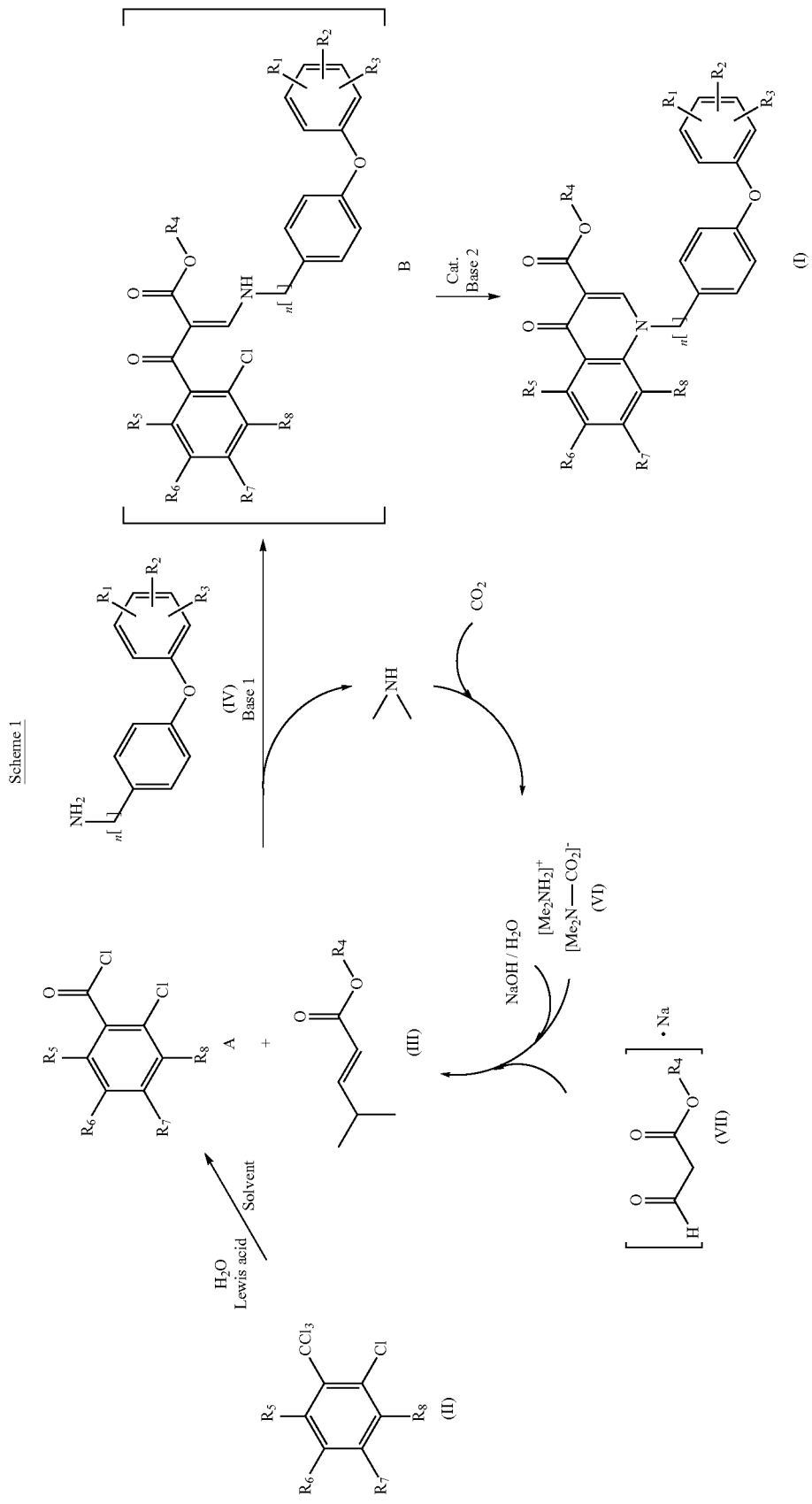
Scheme 1

In the solution of the present disclosure, the Lewis acid in step a) is selected from $FeCl_3$, $FeBr_3$ or $AlCl_3$, and the molar ratio of formula (II) to water is 1:(1-10);

Preferably, the Lewis acid is selected from $FeCl_3$, and the molar ratio of formula (II) to water is 1:(3-6);

In the solution of the present disclosure, the acid binding agent ① in step a) is selected from organic bases, including the following structural formula (V):

wherein $R_9$, $R_{10}$ and $R_{11}$ are selected from hydrogen (H), a methyl group (Methyl), an ethyl group (Ethyl), a n-propyl group (n-Propyl), an isoproyl group (i-Propyl), a n-butyl group (n-Butyl), an isobutyl group (i-Butyl), a tert-butyl group (t-Butyl), or a combination of two or three thereof;

The organic base is also selected from pyridine, 4-dimethylaminopyridine (DMAP), N,N-diisopropylethylamine (DIEA), 1,8-diazabicycloundecyl-7-ene (DBU), tetramethylethylenediamine;

Preferably, $R_9$, $R_{10}$ and $R_{11}$ are selected from an ethyl group (Ethyl), a n-propyl group (n-Propyl), an isoproyl group (i-Propyl), a n-butyl group (n-Butyl), an isobutyl group (i-Butyl), pyridine, 4-dimethylaminopyridine (DMAP);

More preferably, $R_9$, $R_{10}$ and $R_{11}$ are selected from an ethyl group (Ethyl), a n-butyl group (n-Butyl) or 4-dimethylaminopyridine (DMAP);

In the solution of the present disclosure, the solvent in step a) is selected from benzene, toluene, xylene, chlorobenzene, dichlorobenzene, tetrahydrofuran, 1,4-dioxane, N,N-dimethylformamide, N,N-dimethylacetamide, N-methylpyrrolidone, dimethyl sulfoxide, sulfolane, hexamethylphosphorylamine, acetonitrile, diethylene glycol dimethyl ether or a combination of two or more thereof.

Preferably, the solvent is selected from chlorobenzene, N,N-dimethylformamide, N,N-dimethylacetamide, N-methylpyrrolidone, dimethyl sulfoxide, sulfolane;

More preferably, the solvent is selected from N-methylpyrrolidone or dimethyl sulfoxide;

In the solution of the present disclosure, the acid binding agent ② in step b) is selected from inorganic bases, including lithium hydroxide, sodium hydroxide, potassium hydroxide, sodium carbonate, potassium carbonate, cesium carbonate, sodium bicarbonate, potassium bicarbonate;

Preferably, the acid binding agent ② is selected from inorganic bases, including sodium carbonate or potassium carbonate;

In the solution of the present disclosure, the catalyst in step b) is a supported tungsten iron composite catalyst of a core-shell structure, $WO_3/SiO_2/Fe_3O_4$, and the ratio of raw materials ammonium metatungstate, tetraethoxysilane (TEOS) and $Fe_3O_4$ is 1:(10-100):(1-20).

In the solution of the present disclosure, the support of the supported catalyst in step c) is chitosan, and the metal catalyst is nickel acetate [$Ni(OAc)_2$], nickel sulfate ($NiSO_4$), nickel chloride ($NiCl_2$), nickel bromide ($NiBr_2$) or nickel iodide ($NiI_2$). The supported catalysts are CS@$Ni(OAc)_2$, CS@$NiSO_4$, CS@$NiCl_2$, CS@$NiBr_2$ and CS@$NiI_2$, and the mass ratio of the catalyst to formula (II) is 1:(1.0-20).

Preferably, the mass ratio of metal salt to chitosan in the supported catalyst is 1:(20-50).

In the solution of the present disclosure, the molar ratio of the selected formulas (II), (III), (IV), Lewis acid, acid binding agent ① and acid binding agent ② in the preparation process is 1:(1-3.0):(1-3.0):(0.05-1.0):(1.0-5.0):(1.0-5.0).

Preferably, the molar ratio of formula (II), (III), (IV), Lewis acid, acid binding agent ① and acid binding agent ② is 1:(1-1.1.5):(1-1.5):(0.1-0.5):(1.0-3.0):(1.0-3.0).

In the solution of the present disclosure, the reaction conditions of reaction step a are: reaction for 0-3 hours at 0-100° C.; the reaction conditions of reaction step b are: reaction for 1-10 hours at 0-100° C.; the reaction conditions of reaction step c are: reaction for 1-20 hours at 0-150° C.

Preferably, the reaction conditions of reaction step a) are: reaction for 0-2 hours at 50-80° C.; the reaction conditions of reaction step b) are: reaction for 3-6 hours at 10-30° C.; the reaction conditions of reaction step c) are: reaction for 3-10 hours at 60-100° C.

The new quinolone derivatives (I) prepared by the present disclosure have the application of antibacterial activity and can inhibit the activity of Gram-positive bacteria, the Gram-positive bacteria including *Bacillus subtilis, Staphylococcus aureus, Aspergillus fumigatus*, etc., and in particular, have good inhibitory effect on methicillin-resistant *Staphylococcus aureus* (MRSA).

They are suitable for inhibiting the activity of *Bacillus subtilis*.

The new quinolone derivatives (I) prepared by the present disclosure also have the application of anti-tumor cell activity. The anti-tumor cells include non-small cell lung cancer cells (HCC827), lung cancer cells (A549) and liver cancer cells (HepG2), and they are particularly suitable for inhibiting the activity of non-small cell lung cancer cells (HCC827).

Compared with the prior art, the beneficial effects of the present disclosure are mainly shown in: Firstly, the present disclosure innovates the structure of quinolones, introduces the diphenyl ether structural unit into quinolones through C—N bond by using the bioactive molecule splicing method, prepares a series of new quinolone derivatives which expands the scope of the structure, and carries out bioassays to obtain activity data; secondly, the preparation of the series of derivatives is successfully realized by introducing efficient acid binding agents and catalysts and using the existing "one-pot method" technology, avoiding the separation and purification of intermediate products, reducing the reaction procedures, greatly shortening the reaction time and improving the production efficiency.

DESCRIPTION OF THE EMBODIMENTS

The present disclosure is further described in combination with specific embodiments, but the protection scope of the present disclosure is not limited thereto:

The substances concerned in the present disclosure are various, but the preparation methods are similar with the only difference in the replacement of relevant groups, so the embodiments are illustrated when $R_3$, $R_5$ and $R_8$ are selected preferably from hydrogen; $R_4$ is selected from hydrogen, a methyl group or an ethyl group; $R_6$ is fluoro and $R_7$ is chloro. The prepared quinolone derivatives (I) are shown in Table 1 hereinbelow:

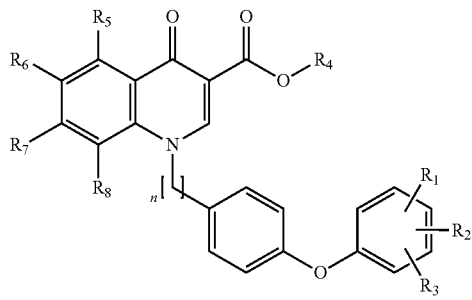

(I)

TABLE 1

Compound library

| Compound | n | $R_1$ | $R_2$ | $R_3$ | $R_4$ | $R_5$ | $R_6$ | $R_7$ | $R_8$ |
|---|---|---|---|---|---|---|---|---|---|
| I-1 | 0 | o-Cl | H | H | Et | H | F | Cl | H |
| I-2 | 0 | m-Cl | H | H | Et | H | F | Cl | H |
| I-3 | 0 | p-Cl | H | H | Et | H | F | Cl | H |
| I-4 | 0 | H | H | H | Et | H | F | Cl | H |
| I-5 | 0 | m-Br | H | H | Et | H | F | Cl | H |
| I-6 | 0 | p-Br | H | H | Et | H | F | Cl | H |
| I-7 | 0 | p-F | H | H | Et | H | F | Cl | H |
| I-8 | 0 | p-Me | H | H | Et | H | F | Cl | H |
| I-9 | 0 | p-Et | H | H | Et | H | F | Cl | H |
| I-10 | 0 | p-(t-Bu) | H | H | Et | H | F | Cl | H |
| I-11 | 0 | p-OCH$_3$ | H | H | Et | H | F | Cl | H |
| I-12 | 0 | p-OCF$_3$ | H | H | Et | H | F | Cl | H |
| I-13 | 0 | p-NO$_2$ | H | H | Et | H | F | Cl | H |
| I-14 | 0 | p-CF$_3$ | H | H | Et | H | F | Cl | H |
| I-15 | 0 | m-Cl | p-Cl | H | Et | H | F | Cl | H |
| I-16 | 0 | m-F | p-F | H | Et | H | F | Cl | H |
| I-17 | 0 | m-Me | p-Me | H | Et | H | F | Cl | H |
| I-18 | 0 | o-Cl | p-Cl | H | Et | H | F | Cl | H |
| I-19 | 0 | m-CF$_3$ | p-CF$_3$ | H | Et | H | F | Cl | H |
| I-20 | 1 | p-Cl | H | H | Et | H | F | Cl | H |
| I-21 | 1 | p-F | H | H | Et | H | F | Cl | H |
| I-22 | 1 | o-Me | H | H | Et | H | F | Cl | H |
| I-23 | 1 | p-(t-Bu) | H | H | Et | H | F | Cl | H |
| I-24 | 1 | m-Cl | p-Cl | H | Et | H | F | Cl | H |
| I-25 | 1 | m-Me | p-Me | H | Et | H | F | Cl | H |
| I-26 | 0 | p-Cl | H | H | H | H | F | Cl | H |
| I-27 | 0 | p-Me | H | H | H | H | F | Cl | H |
| I-28 | 0 | p-OCH$_3$ | H | H | H | H | F | Cl | H |
| I-29 | 0 | p-OCF$_3$ | H | H | H | H | F | Cl | H |
| I-30 | 1 | m-CF$_3$ | p-CF$_3$ | H | H | H | F | Cl | H |

Since the substances concerned in the present disclosure are various, but the preparation methods are similar with the only difference in the replacement of relevant groups, only a few representative compounds are selected to describe their preparation, which is specifically illustrated as follows:

Example 1: Preparation of ethyl 7-chloro-1-(4-(4-chlorophenoxy)phenyl)-6-fluoro-4-oxy-1,4-dihydro-quinoline-3-carboxylate (Compound I-3)

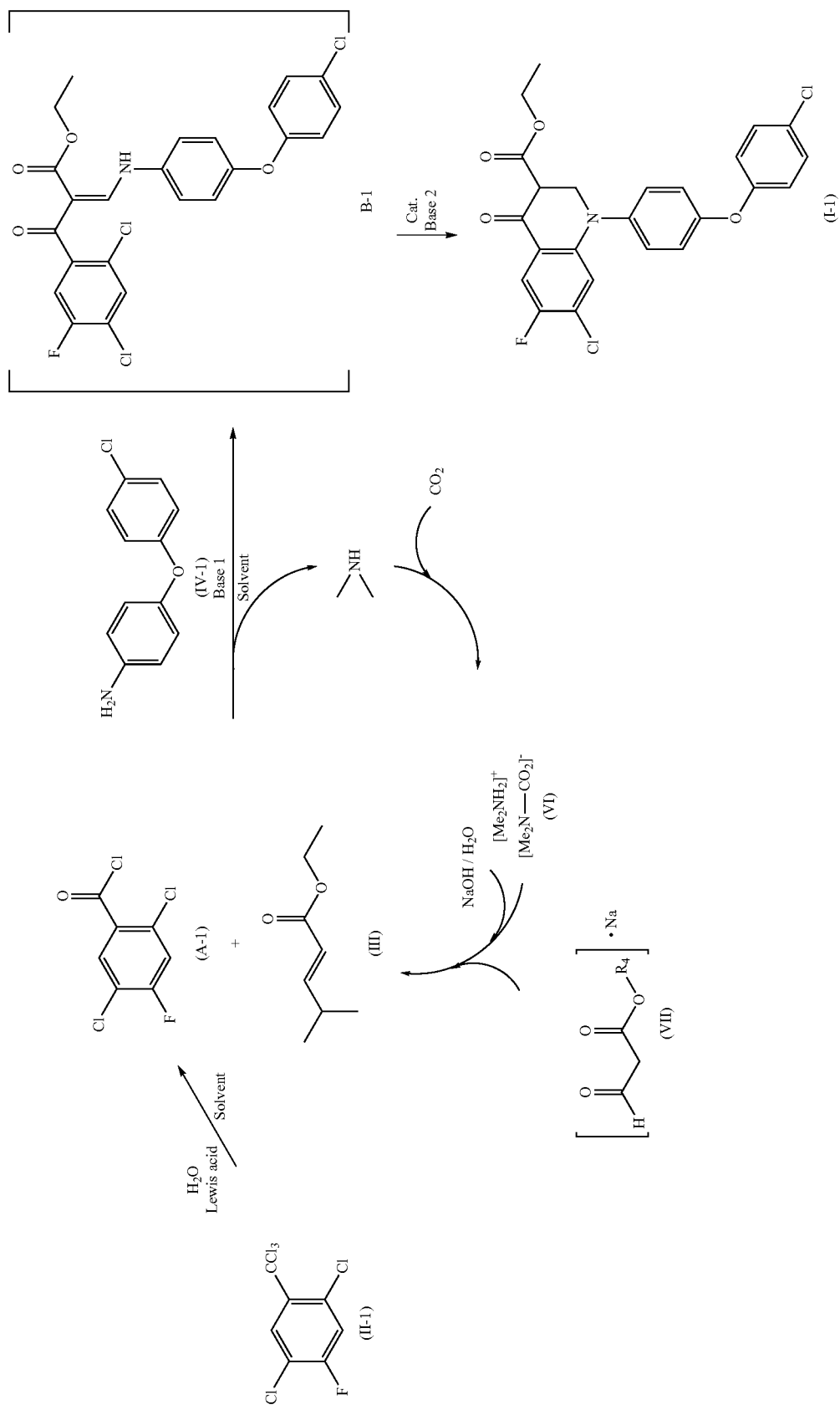

a) To a 100 ml three-necked flask are added II-1 (2.82 g, 10 mmol), ferric chloride (0.16 g, 1 mmol), purified water (0.54 g, 30 mmol) and solvent N,N-dimethylacetamide (30 g); the temperature is increased to 80° C. under magnetic stirring, and the temperature is maintained for 1 hour to obtain intermediate A;

b) To the above reaction solution are added formula (III) (1.71 g, 12 mmol) and triethylamine (2.02 g, 20 mmol); the temperature is kept at 30° C. for 3 hours, and the reaction is tracked by TLC until A is completely converted; then formula (IV-3) (2.20 g, 10 mmol) is added; the temperature is increased to 60° C. and maintained for 3 hours;

c) To the above reaction solution are added potassium carbonate (2.76 g, 20 mmol) and a core-shell supported tungsten composite catalyst $WO_3/SiO_2/Fe_3O_4$ (0.45 g); the temperature is increased to 100° C., and the reaction is carried out for 6 hours to complete the reaction. After cooling to room temperature, 150 g purified water is added, followed by filtration and oven-drying to obtain 4.05 g light yellow solid, which afford the target product I-3 after recrystallization with 5% aqueous solution of ethanol, 3.26 g white powder, with a theoretical yield of 4.72 g and a total recovery rate of 69.1%.

$^1$H NMR (CDCl$_3$, 600 MHz): δ 8.46 (s, 1H), 8.21 (d, J=12 Hz, 1H), 7.42-7.40 (m, 4H), 7.20 (d, J=12 Hz, 2H), 7.11-7.07 (m, 3H), 4.38 (q, J=6 Hz, 2H), 1.39 (t, J=6 Hz, 3H).

Example 2: Preparation of ethyl 7-chloro-6-fluoro-4-oxy-1-(4-phenoxyphenyl)-1,4-dihydroquinoline-3-carboxylate (Compound I-4)

The operation steps of this example are the same as those of Example 1, while the difference is that the reaction solvent in the preparation process is changed from N,N-dimethylacetamide in Example 1 to toluene.

a) To a 100 ml three-necked flask are added II-1 (2.82 g, 10 mmol), ferric chloride (0.16 g, 1 mmol), purified water (0.54 g, 30 mmol) and solvent toluene (30 g); the temperature is increased to 80° C. under magnetic stirring, and the temperature is maintained for 1 hour to obtain intermediate A;

b) To the above reaction solution are added formula (III) (1.71 g, 12 mmol) and triethylamine (2.02 g, 20 mmol); the temperature is kept at 30° C. for 3 hours, and the reaction is tracked by TLC until A is completely converted; then formula IV-4 (1.85 g, 10 mmol) is added; the temperature is increased to 60° C. and maintained for 3 hours;

c) To the above reaction solution are added potassium carbonate (2.76 g, 20 mmol) and a core-shell supported tungsten composite catalyst $WO_3/SiO_2/Fe_3O_4$ (0.45 g); the temperature is increased to 100° C., and the reaction is carried out for 6 hours to complete the reaction. After cooling to room temperature, 150 g purified water is added, followed by filtration and oven-drying to obtain 3.85 g light yellow solid, which afford the target product I-4 after recrystallization with 5% aqueous solution of ethanol, 2.80 g white powder, with a theoretical yield of 4.38 g and a total recovery rate of 63.9%.

Example 3: Preparation of ethyl 7-chloro-6-fluoro-1-(4-(4-fluorophenoxy)phenyl)-4-oxy-1,4-dihydro-quinoline-3-carboxylate (Compound I-7)

The operation steps of this example are the same as those of Example 1, while the difference is that the reaction solvent in the preparation process is changed from N,N-dimethylacetamide in Example 1 to 1,4-dioxane.

a) To a 100 ml three-necked flask are added II-1 (2.82 g, 10 mmol), ferric chloride (0.16 g, 1 mmol), purified water (0.54 g, 30 mmol) and solvent 1,4-dioxane (30 g); the temperature is increased to 80° C. under magnetic stirring, and the temperature is maintained for 1 hour to obtain intermediate A;

b) To the above reaction solution are added formula (III) (1.71 g, 12 mmol) and triethylamine (2.02 g, 20 mmol); the temperature is kept at 30° C. for 3 hours, and the reaction is tracked by TLC until A is completely converted; then formula IV-7 (2.03 g, 10 mmol) is added; the temperature is increased to 60° C. and maintained for 3 hours;

c) To the above reaction solution are added potassium carbonate (2.76 g, 20 mmol) and a core-shell supported tungsten composite catalyst $WO_3/SiO_2/Fe_3O_4$ (0.45 g); the temperature is increased to 100° C., and the reaction is carried out for 6 hours to complete the reaction. After cooling to room temperature, 150 g purified water is added, followed by filtration and oven-drying to obtain 3.35 g pale brown solid, which afford the target product I-7 after recrystallization with 5% aqueous solution of ethanol, 2.10 g pale brown solid, with a theoretical yield of 4.56 g and a total recovery rate of 46.1%.

Example 4: Preparation of ethyl 7-chloro-6-fluoro-1-(4-(4-toluoxy)phenyl)-4-oxy-1,4-dihydroquinoline-3-carboxylate (Compound I-8)

The operation steps of this example are the same as those of Example 1, while the difference is that the reaction solvent in the preparation process is changed from N,N-dimethylacetamide in Example 1 to dimethyl sulfoxide.

a) To a 100 ml three-necked flask are added II-1 (2.82 g, 10 mmol), ferric chloride (0.16 g, 1 mmol), purified water (0.54 g, 30 mmol) and solvent dimethyl sulfoxide (30 g); the temperature is increased to 80° C. under magnetic stirring, and the temperature is maintained for 1 hour to obtain intermediate A;

b) To the above reaction solution are added formula (III) (1.71 g, 12 mmol) and triethylamine (2.02 g, 20 mmol); the temperature is kept at 30° C. for 3 hours, and the reaction is tracked by TLC until A is completely converted; then formula IV-8 (2.0 g, 10 mmol) is added; the temperature is increased to 60° C. and maintained for 3 hours;

c) To the above reaction solution are added potassium carbonate (2.76 g, 20 mmol) and a core-shell supported tungsten composite catalyst $WO_3/SiO_2/Fe_3O_4$ (0.45 g); the temperature is increased to 100° C., and the reaction is carried out for 6 hours to complete the reaction. After cooling to room temperature, 150 g purified water is added, followed by filtration and oven-drying to obtain 4.35 g beige-yellow solid, which afford the target product I-8 after recrystallization with 5% aqueous solution of ethanol, 3.15 g light yellow solid, with a theoretical yield of 4.52 g and a total recovery rate of 69.7%.

Example 5: Preparation of ethyl 7-chloro-6-fluoro-1-(4-(4-tert-butylphenoxy)phenyl)-4-oxy-1,4-dihydroquinoline-3-carboxylate (Compound I-10)

The operation steps of this example are the same as those of Example 1, while the difference is that the acid binding agent ① in the preparation process is changed from triethylamine in Example 1 to tri-n-butylamine.

a) To a 100 ml three-necked flask are added II-1 (2.82 g, 10 mmol), ferric chloride (0.16 g, 1 mmol), purified water (0.54 g, 30 mmol) and solvent dimethyl sulfoxide (30 g); the temperature is increased to 80° C. under magnetic stirring, and the temperature is maintained for 1 hour to obtain intermediate A;

b) To the above reaction solution are added formula (III) (1.71 g, 12 mmol) and tri-n-butylamine (3.71 g, 20 mmol); the temperature is kept at 30° C. for 3 hours, and the reaction is tracked by TLC until A is completely converted; then formula IV-10 (2.41 g, 10 mmol) is added; the temperature is increased to 60° C. and maintained for 3 hours;

c) To the above reaction solution are added potassium carbonate (2.76 g, 20 mmol) and a core-shell supported tungsten composite catalyst $WO_3/SiO_2/Fe_3O_4$ (0.45 g); the temperature is increased to 100° C., and the reaction is carried out for 6 hours to complete the reaction. After cooling to room temperature, 150 g purified water is added, followed by filtration and oven-drying to obtain 3.75 g light yellow solid, which afford the target product I-10 after recrystallization with 5% aqueous solution of ethanol, 3.05 g light yellow solid, with a theoretical yield of 4.94 g and a total recovery rate of 61.7%.

Example 6: Preparation of ethyl 7-chloro-6-fluoro-1-(4-(4-methoxyphenoxy)phenyl)-4-oxy-1,4-dihydroquinoline-3-carboxylate (Compound I-11)

The operation steps of this example are the same as those of Example 1, while the difference is that the acid binding agent ① in the preparation process is changed from triethylamine in Example 1 to 4-dimethylaminopyridine.

a) To a 100 ml three-necked flask are added II-1 (2.82 g, 10 mmol), ferric chloride (0.16 g, 1 mmol), purified water (0.54 g, 30 mmol) and solvent dimethyl sulfoxide (30 g); the temperature is increased to 80° C. under magnetic stirring, and the temperature is maintained for 1 hour to obtain intermediate A;

b) To the above reaction solution are added formula (III) (1.71 g, 12 mmol) and 4-dimethylaminopyridine (DMAP, 2.44 g, 20 mmol); the temperature is kept at 30° C. for 3 hours, and the reaction is tracked by TLC until A is completely converted; then formula IV-11 (2.15 g, 10 mmol) is added; the temperature is increased to 60° C. and maintained for 3 hours;

c) To the above reaction solution are added potassium carbonate (2.76 g, 20 mmol) and a core-shell supported tungsten composite catalyst $WO_3/SiO_2/Fe_3O_4$ (0.45 g); the temperature is increased to 100° C., and the reaction is carried out for 6 hours to complete the reaction. After cooling to room temperature, 150 g purified water is added, followed by filtration and oven-drying to obtain 3.80 g light yellow solid, which afford the target product I-11 after recrystallization with 5% aqueous solution of ethanol, 2.85 g white solid, with a theoretical yield of 4.68 g and a total recovery rate of 60.9%.

$^1H$ NMR (CDCl$_3$, 600 MHz): δ 8.46 (s, 1H), 8.21 (d, J=9.0 Hz, 1H), 7.35-7.33 (m, 2H), 7.14-7.08 (m, 5H), 6.98-6.97 (m, 2H), 4.38 (q, J=7.2 Hz, 2H), 3.85 (s, 3H), 1.39 (t, J=7.2 Hz, 3H).

Example 7: Preparation of ethyl 7-chloro-6-fluoro-1-(4-(4-trifluoromethoxyphenoxy) phenyl)-4-oxy-1,4-dihydroquinoline-3-carboxylate (Compound I-12)

The operation steps of this example are the same as those of Example 1, while the difference is that the acid binding agent ② in the preparation process is changed from potassium carbonate in Example 1 to sodium carbonate.

a) To a 100 ml three-necked flask are added II-1 (2.82 g, 10 mmol), ferric chloride (0.16 g, 1 mmol), purified water (0.54 g, 30 mmol) and solvent dimethyl sulfoxide (30 g); the temperature is increased to 80° C. under magnetic stirring, and the temperature is maintained for 1 hour to obtain intermediate A;

b) To the above reaction solution are added formula (III) (1.71 g, 12 mmol) and triethylamine (2.02 g, 20 mmol); the temperature is kept at 30° C. for 3 hours, and the reaction is tracked by TLC until A is completely converted; then formula IV-12 (2.69 g, 10 mmol) is added; the temperature is increased to 60° C. and maintained for 3 hours;

c) To the above reaction solution are added sodium carbonate (2.12 g, 20 mmol) and a core-shell supported tungsten composite catalyst $WO_3/SiO_2/Fe_3O_4$ (0.45 g); the temperature is increased to 100° C., and the reaction is carried out for 6 hours to complete the reaction. After cooling to room temperature, 150 g purified water is added, followed by filtration and oven-drying to obtain 4.10 g light yellow solid, which afford the target product I-12 after recrystallization with 5% aqueous solution of ethanol, 3.35 g white solid, with a theoretical yield of 5.22 g and a total recovery rate of 64.2%.

Example 8: Preparation of ethyl 7-chloro-6-fluoro-1-(4-(4-trifluoromethylphenoxy) phenyl)-4-oxy-1,4-dihydroquinoline-3-carboxylate (Compound I-14)

The operation steps of this example are the same as those of Example 1, while the difference is that the acid binding agent ② in the preparation process is changed from potassium carbonate in Example 1 to sodium hydroxide.

a) To a 100 ml three-necked flask are added II-1 (2.82 g, 10 mmol), ferric chloride (0.16 g, 1 mmol), purified water (0.54 g, 30 mmol) and solvent dimethyl sulfoxide (30 g); the temperature is increased to 80° C. under magnetic stirring, and the temperature is maintained for 1 hour to obtain intermediate A;

b) To the above reaction solution are added formula (III) (1.71 g, 12 mmol) and triethylamine (2.02 g, 20 mmol); the temperature is kept at 30° C. for 3 hours, and the reaction is tracked by TLC until A is completely converted; then formula IV-14 (2.53 g, 10 mmol) is added; the temperature is increased to 60° C. and maintained for 3 hours;

c) To the above reaction solution are added sodium hydroxide (0.8 g, 20 mmol) and a core-shell supported tungsten composite catalyst $WO_3/SiO_2/Fe_3O_4$ (0.45 g); the temperature is increased to 100° C., and the reaction is carried out for 6 hours to complete the reaction. After cooling to room temperature, 150 g purified water is added, followed by filtration and oven-drying to obtain 3.35 g yellow solid, which afford the target product I-14 after recrystallization with 5% aqueous solution of ethanol, 2.32 g light yellow solid, with a theoretical yield of 5.06 g and a total recovery rate of 45.8%.

Example 9: Preparation of ethyl 7-chloro-1-(4-(3,4-dichlorophenoxy)phenyl)-6-fluoro-4-oxy-1,4-dihydroquinoline-3-carboxylate (Compound I-15)

The operation steps of this example are the same as those of Example 1, while the difference is that the amount of the acid binding agent ① in the preparation process is changed from (2.02 g, 20 mmol) in Example 1 to (1.21 g, 12 mmol).

a) To a 100 ml three-necked flask are added II-1 (2.82 g, 10 mmol), ferric chloride (0.16 g, 1 mmol), purified water (0.54 g, 30 mmol) and solvent dimethyl sulfoxide (30 g); the temperature is increased to 80° C. under magnetic stirring, and the temperature is maintained for 1 hour to obtain intermediate A;

b) To the above reaction solution are added formula (III) (1.71 g, 12 mmol) and triethylamine (1.21 g, 12 mmol); the temperature is kept at 30° C. for 3 hours, and the reaction is tracked by TLC until A is completely converted; then formula IV-15 (2.54 g, 10 mmol) is added; the temperature is increased to 60° C. and maintained for 3 hours;

c) To the above reaction solution are added potassium carbonate (2.76 g, 20 mmol) and a core-shell supported tungsten composite catalyst $WO_3/SiO_2/Fe_3O_4$ (0.45 g); the temperature is increased to 100° C., and the reaction is carried out for 6 hours to complete the reaction. After cooling to room temperature, 150 g purified water is added, followed by filtration and oven-drying to obtain 4.05 g light yellow solid, which afford the target product I-15 after recrystallization with 5% aqueous solution of ethanol, 3.32 g light yellow solid, with a theoretical yield of 5.07 g and a total recovery rate of 65.5%.

$^1$H NMR (CDCl$_3$, 600 MHz): δ 8.46 (s, 1H), 8.21 (d, J=8.4 Hz, 1H), 7.51 (d, J=9.0 Hz, 1H), 7.45 (d, J=9.0 Hz, 2H), 7.27-7.23 (m, 3H), 7.07 (d, J=6.0 Hz, 1H), 7.04-7.02 (m, 1H), 4.38 (q, J=7.2 Hz, 2H), 1.39 (t, J=7.2 Hz, 3H).

Example 10: Preparation of ethyl 7-chloro-1-(4-(3,4-dimethylphenoxyl)phenyl)-6-fluoro-4-oxy-1,4-dihydroquinoline-3-carboxylate (Compound I-17)

The operation steps of this example are the same as those of Example 1, while the difference is that the temperature of step c) in the preparation process is changed from 100° C. in Example 1 to 60° C.

a) To a 100 ml three-necked flask are added II-1 (2.82 g, 10 mmol), ferric chloride (0.16 g, 1 mmol), purified water (0.54 g, 30 mmol) and solvent dimethyl sulfoxide (30 g); the temperature is increased to 80° C. under magnetic stirring, and the temperature is maintained for 1 hour to obtain intermediate A;

b) To the above reaction solution are added formula (III) (1.71 g, 12 mmol) and triethylamine (2.02 g, 20 mmol); the temperature is kept at 30° C. for 3 hours, and the reaction is tracked by TLC until A is completely converted; then formula IV-17 (2.13 g, 10 mmol) is added; the temperature is increased to 60° C. and maintained for 3 hours;

c) To the above reaction solution are added potassium carbonate (2.76 g, 20 mmol) and a core-shell supported tungsten composite catalyst $WO_3/SiO_2/Fe_3O_4$ (0.45 g); the temperature is increased to 60° C., and the reaction is carried out for 6 hours to complete the reaction. After cooling to room temperature, 150 g purified water is added, followed by filtration and oven-drying to obtain 3.80 g beige-yellow solid, which afford the target product I-17 after recrystallization with 5% aqueous solution of ethanol, 2.74 g white solid, with a theoretical yield of 4.66 g and a total recovery rate of 58.8%.

Example 11: Preparation of ethyl 7-chloro-1-(4-(4-chlorophenoxy)benzyl)-6-fluoro-4-oxy-1,4-dihydro-quinoline-3-carboxylate (Compound I-20)

The operation steps and feeding amount of this example are the same as those of Example 1, leading to the obtaining of 3.90 g crude product, which afford the target product I-20 after recrystallization with 5% aqueous solution of ethanol, 3.50 g white solid, with a theoretical yield of 4.86 g and a total recovery rate of 72.0%.

Example 12: Preparation of ethyl 7-chloro-1-(4-(2-methylphenoxy)benzyl)-6-fluoro-4-oxy-1,4-dihydro-quinoline-3-carboxylate (Compound I-22)

The operation steps and feeding amount of this example are the same as those of Example 1, leading to the obtaining of 3.50 g beige-yellow crude product, which afford the target product I-22 after recrystallization with 5% aqueous solution of ethanol, 3.05 g white solid, with a theoretical yield of 4.66 g and a total recovery rate of 65.5%.

Example 13: Preparation of 7-chloro-1-(4-(4-chlorophenoxy)phenyl)-6-fluoro-4-oxy-1,4-dihydroquinoline-3-carboxylic acid (Compound I-26)

Compound I-3 prepared in the above Example 1 is used as raw material, and the specific implementation process is as follows:

Compound I-3 (1.89 g, 4 mmol) and 5% sodium hydroxide solution (16.0 g) are added to a 50 ml one-neck glass bottle; refluxing is carried out under magnetic stirring at an elevated temperature for 3 hours; the reaction solution becomes clear. After cooling to below 30° C., 15% of hydrochloric acid is added dropwise such that the solution is adjusted to be neutral; the solution is filtered; the filter cake is dried in vacuum to obtain 1.47 g white powder, which is Compound I-20, with a theoretical yield of 1.78 g and a recovery rate of 82.6%.

$^1$H NMR (CDCl$_3$, 600 MHz): δ4.37 (brs, 1H), 8.76 (s, 1H), 8.28 (d, J=8.4 Hz, 1H), 7.44-7.42 (m, 2H), 7.38-7.36 (m, 2H), 7.25-7.21 (m, 3H), 7.12-7.10 (m, 2H).

Example 14: Preparation of 7-chloro-1-(4-(4-methoxyphenoxy)phenyl)-6-fluoro-4-oxy-1,4-dihydroquinoline-3-carboxylic acid (Compound I-28)

Compound I-11 prepared in the above Example 1 is used as raw material, and the method is the same as that of Example 13 with a difference in that the concentration of sodium hydroxide in the preparation process is changed from 16.0 g of a 5% solution in Example 13 to 16.0 g of a 10% solution.

The feeding amount of compound I-11 is 1.87 g, 4 mmol. 1.34 g white powder is obtained, which is Compound I-28 with a theoretical yield of 1.76 g and a recovery rate of 76.1%.

$^1$H NMR (DMSO-d$_6$, 600 MHz): δ4.79 (brs, 0.51H), 8.61 (s, 1H), 8.20 (d, J=8.4 Hz, 1H), 7.58-7.56 (m, 2H), 7.13-7.01 (m, 7H).

Example 15: Preparation of 7-chloro-1-(4-(4-trifluoromethoxyphenoxy)phenyl)-6-fluoro-4-ox-1,4-dihydroquinoline-3-carboxylic acid (Compound I-29)

Compound I-12 prepared in the above Example 1 is used as raw material, and the method is the same as that of Example 13 with a difference in that the refluxing time of the reaction in the preparation process is changed from 3 hours in Example 13 to 6 hours.

The feeding amount of Compound I-12 is 2.09 g, 4 mmol. 1.48 g white powder is obtained, which is Compound I-29 with a theoretical yield of 2.08 g and a recovery rate of 71.2%.

$^1$H NMR (DMSO-d$_6$, 600 MHz): δ4.65 (brs, 0.32H), 8.67 (s, 1H), 8.21 (d, J=8.4 Hz, 1H), 7.70-7.68 (m, 2H), 7.46-7.44 (m, 2H), 7.33-7.29 (m, 5H).

Example 16: Bactericidal Activity Test

In order to determine the practicability of the compounds synthesized in this patent, some of the compounds are selected as representatives, and the bactericidal activity is determined by conventional methods. The specific operation procedures are as follows:

In a super clean bench, the preserved strains are transferred to a slant tube, cultured in an incubator at 37° C. for 24 hours, and then taken out and preserved at low temperature for antibacterial experiments. The well-grown colonies are scraped and transferred into a liquid medium with the inoculation ring, shaken to give a uniform mixture, and cultured in the incubator at 37° C. for 24 hours. The culture medium is poured into plates, about 15 ml for each plate, which are placed horizontally, and after solidification, placed upside down into the incubator at 37° C.; after two days, it is observed whether there is colony growth. If not, it can be used for the next experiment, otherwise, the plate needs to be poured again. 0.5 ml of bacterial suspension is pipetted into the plate, which is left to stand still for about 5 minutes, and then spread evenly with a coating rod; two duplicate plates are set for each kind of bacteria. In the super clean bench, the plates are divided equally and parallel groups are set. Each piece of filter paper (6 mm in diameter) is a paste. The filter paper is picked up with tweezers, dipped into a sample, taken out, placed at a given position of the plate, and gently pressed to make the filter paper firmly adhered thereto. The plate is placed (upside down) in the incubator for culture; the temperature is set at 37° C.; and after 24 hours culture, the plate is observed and the results are recorded. Specific results are shown in Table 2:

TABLE 2

| Antibacterial activity test | | | | | | | | |
|---|---|---|---|---|---|---|---|---|
| Tested bacteria | Cpd 3[a] | Cpd 4 | Cpd 7 | Cpd 8 | Cpd 10 | Cpd 11 | Cpd 12 | Cpd 14 |
| S. aureus inhibition zone (mm) | 20 | 19 | 15 | 13 | 20 | 11 | 24 | 20 |
| E. coli activity inhibition zone (mm) | 24 | 27 | 17 | 12 | 24 | 22 | 28 | 27 |
| B. subtilis inhibition zone (mm) | 18 | 23 | 13 | 12 | 20 | 13 | 8 | 15 |
| MRSA inhibition zone[b] (mm) | 8 | 9 | 7 | 10 | 14 | 7 | 8 | 12 |
| Tested bacteria | Cpd 15 | Cpd 17 | Cpd 20 | Cpd 22 | Cpd 26 | Cpd 27 | Cpd 28 | Control group[c] |
| S. aureus activity (mm) | 20 | 20 | 21 | 23 | 29 | 27 | 29 | 26 |
| E. coli activity inhibition zone (mm) | 21 | 29 | 24 | 30 | 29 | 27 | 25 | 25 |
| B. subtilis (mm) | 18 | 11 | 12 | 18 | 24 | 25 | 28 | 22 |
| MRSA inhibition zone[c] (mm) | 9 | 7 | 10 | 14 | 15 | 12 | 11 | 12 |

[a]The diameter of the filter paper is 6 mm, and the sample concentration is 10 mg/mL;
[b]methicillin-resistant *Staphylococcus aureus*;
[c]the control group is levofloxacin hydrochloride*, and the control concentration is 5 mg/mL.

Example 17: Anti-Tumor Activity Test

For the anti-tumor activity test of these compounds, three kinds of common tumor cells are taken as research subjects: non-small cell lung cancer cells (HCC827), lung cancer cells (A549) and liver cancer cells (HepG2). Under the action of the new quinolone derivatives, the growth of the cells is observed, and the proliferation of tumor cells is measured by MTT method.

The specific operation is as follows: the tumor cells are inoculated into 96-well culture plate in a particular amount of cells, with a cell density of $2 \times 10^4$ cells/ml; after overnight in the incubator with a concentration of 5% $CO_2$ at 37° C., the screened samples are added (reference can be made to Table 1 for sample concentration; 10 μL/well of corresponding concentration of drugs are added to the dosing group, while 10 μL/well of PBS are added to the control group). After 44 hours of culture, 10 μL/well of MTT are added to continue the culture for 4 hours, which is dissolved with DMSO, shaken, and detected with a 570 nm enzyme-labeled instrument.

The half inhibitory concentration $IC_{50}$ of the new quinolone derivatives prepared in Examples 1, 7 and 13 and that of the positive drug paclitaxel in the control group against the three tumor cells are tested, and the results of the test are shown in Table 3.

TABLE 3

| Anti-tumor activity test | | | |
|---|---|---|---|
| Cell name | Cpd | Concentration (DMSO as solvent) | $IC_{50}$(μmol/l) |
| HCC827 | I-3 | 0.5 mg/ml | 4.5 |
|  | I-12 | 0.5 mg/ml | >10 |
|  | I-26 | 0.5 mg/ml | 5.0 |
|  | Paclitaxel | 0.5 mg/ml | 2.5 |
| A549 | I-3 | 0.5 mg/ml | >10 |
|  | I-12 | 0.5 mg/ml | >10 |
|  | I-26 | 0.5 mg/ml | >10 |
|  | Paclitaxel | 0.5 mg/ml | 3.5 |
| HepG2 | I-3 | 0.5 mg/ml | 7.5 |
|  | I-12 | 0.5 mg/ml | 8.5 |
|  | I-26 | 0.5 mg/ml | 5.0 |
|  | Paclitaxel | 0.5 mg/ml | 1.5 |

It has been found that the new quinolone derivatives have the function of inhibiting HCC827 (non-small cell lung cancer cells) and HepG2 (human liver cancer cells) tumor cells, but the inhibitory effect on A549 (lung cancer cells) is not significant. There is a gap compared with paclitaxel, a positive drug which is currently used for inhibiting the tumor cells, but this can also reflect that the new quinolones derivatives as designed have inhibitory function, and may also have inhibitory activity for other tumor cells, and have an application prospect.

What is claimed is:

1. A compound of formula (I):

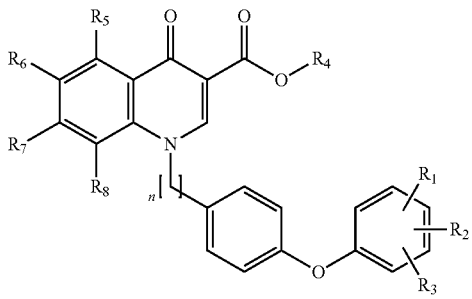

wherein n represents a number of 0 or 1;

$R_1$ represents hydrogen, a $C_1$-$C_6$ alkyl group, a $C_1$-$C_6$ alkoxy group, a $C_1$-$C_6$ alkyloxy group, halogen, a nitro group, a trifluoromethyl group, a trifluoromethoxy group;

$R_2$ represents hydrogen, a $C_1$-$C_6$ alkyl group, halogen;

$R_3$ represents hydrogen;

$R_4$ is selected from hydrogen, a $C_1$-$C_6$ alkyl group, a $C_5$-$C_6$ cycloakyl group, a phenyl group, a substituted phenyl group, a benzyl group or a substituted benzyl;

$R_5$, $R_6$, $R_7$ and $R_8$ are hydrogen, a $C_1$-$C_3$ alkyl group, halogen, a cyano group or a nitro group.

2. The quinolone derivative according to claim 1, characterized in that it corresponds to formula (I-a):

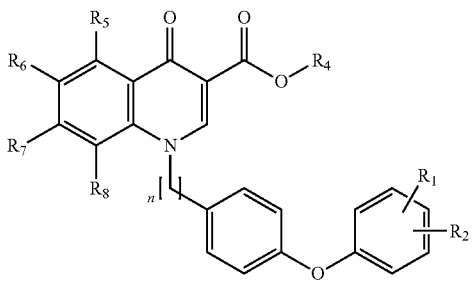

wherein n represents a number of 0 or 1;

$R_1$ represents hydrogen, a $C_1$-$C_6$ alkyl group, a $C_1$-$C_6$ alkoxy group, halogen, a nitro group, a trifluoromethyl group, a trifluoromethoxy group;

$R_2$ represents hydrogen, a $C_1$-$C_6$ alkyl group, halogen;

$R_4$ is selected from hydrogen, a methyl group, an ethyl group, a n-propyl group, an isopropyl group, a n-butyl group, an isobutyl group, a tert-butyl group, a phenyl group;

$R_6$, $R_7$ and $R_8$ are hydrogen, halogen, a cyano group or a nitro group.

3. The compound of formula (I) according to claim 2, characterized in that it corresponds to formula (I-b):

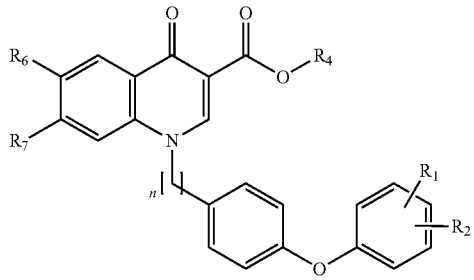

wherein n represents a number of 0 or 1;

$R_1$ represents hydrogen, a $C_1$-$C_6$ alkyl group, a $C_1$-$C_6$ alkoxy group, halogen, a nitro group, a trifluoromethyl group, a trifluoromethoxy group;

$R_2$ represents hydrogen, a $C_1$-$C_6$ alkyl group, halogen;

$R_4$ is selected from hydrogen, a methyl group, an ethyl group;

$R_5$, $R_8$ represent hydrogen;

$R_6$ is fluoro;

$R_7$ is chloro.

4. The compound of formula (I) according to claim 1, the preparation method thereof comprising the following steps:

reacting formula (II) with water in an organic solvent under the catalysis of a Lewis acid to obtain an intermediate product A;

adding an acid binding agent ① to the reaction system, mixing it with the raw material shown in formula (III) for reaction, then adding a diphenyl ether amine compound shown in formula (IV) for reaction to obtain an intermediate product B, adding a further acid binding agent ② and a supported catalyst to carry out a cyclization reaction to obtain the compound of formula (I), wherein, the acid binding agent ② is selected from inorganic bases, including lithium hydroxide, sodium hydroxide, potassium hydroxide, sodium carbonate, potassium carbonate, cesium carbonate, sodium bicarbonate, potassium bicarbonate,

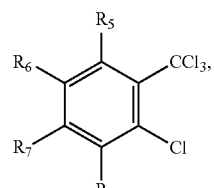

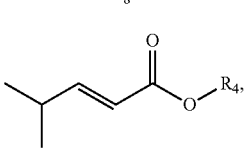

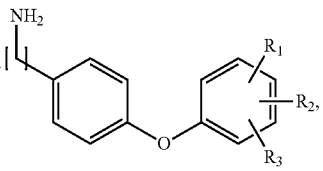

-continued (B)

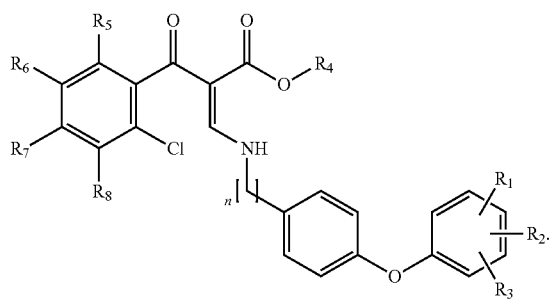

5. The method for preparing the compound of formula (I) according to claim 4, characterized in that the Lewis acid is selected from FeCl$_3$, FeBr$_3$ or AlCl$_3$.

6. The method for preparing the compound of formula (I) according to claim 4, characterized in that the acid binding agent ① is selected from organic bases, including the following structural formula (V):

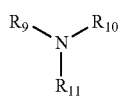

(V)

wherein R$_9$, R$_{10}$ and R$_{11}$ are selected from hydrogen (H), a methyl group (Methyl), an ethyl group (Ethyl), a n-propyl group (n-Propyl), an isoproyl group (i-Propyl), a n-butyl group (n-Butyl), an isobutyl group (i-Butyl), a tert-butyl group (t-Butyl), or a combination of two or three thereof;

the organic base is also selected from pyridine, 4-dimethylaminopyridine (DMAP), N,N-diisopropylethylamine (DIEA), 1,8-diazabicycloundecyl-7-ene (DBU), tetramethylethylenediamine.

7. The method for preparing e compound of formula (I) according to claim 4, characterized in that the solvent is selected from benzene, toluene, xylene, chlorobenzene, dichlorobenzene, tetrahydrofuran, 1,4-dioxane, N,N-dimethylformamide, N,N-dimethylacetamide, N-methylpyrrolidone, dimethyl sulfoxide, sulfolane, hexamethylphosphorylamine, acetonitrile, diethylene glycol dimethyl ether or a combination of two or more thereof.

8. The method for preparing the compound of formula (I) according to claim 4, characterized in that the catalyst is a supported tungsten iron composite catalyst of a core-shell structure, WO$_3$/SiO$_2$/Fe$_3$O$_4$, and the ratio of raw materials ammonium metatungstate, tetraethoxysilane (TEOS) and Fe$_3$O$_4$ is 1:(10-100):(1-20).

9. The method for preparing the compound of formula (I) according to claim 4, characterized in that the support of the supported catalyst is chitosan, and the metal catalyst is nickel acetate [Ni(OAc)$_2$], nickel sulfate (NiSO$_4$), nickel chloride (NiCl$_2$), nickel bromide (NiBr$_2$) or nickel iodide (NiI$_2$), the supported catalysts are CS@Ni(OAc)$_2$, CS@NiSO$_4$, CS@NiCl$_2$, CS@NiBr$_2$ and CS@NiI$_2$, and the mass ratio of the catalyst to for (II) is 1:(1.0-20).

10. The method for preparing the compound of formula (I) according to claim 4, characterized in that the molar ratio of the selected formulas (II), (II), (IV), Lewis acid, acid binding agent ① and acid binding agent ② in the preparation process is 1:(1-3.0):(1-3.0):(0.05-1.0):(1.0-5.0):(1.0-5.0).

11. The method for preparing the compound of formula (I) according to claim 4, characterized in that the reaction conditions of reaction step a are: reaction for 0-3 hours at 0-100° C.; the reaction conditions of reaction step b are: reaction for 1-10 hours at 0-100° C.; the 10 reaction conditions of reaction step c are: reaction for 1-20 hours at 0-150° C.

12. The compound of formula (I) according to claim 1, having the effect of inhibiting bacteria, wherein it has a good inhibitory effect on methicillin-resistant *Staphylococcus aureus* (MRSA).

* * * * *